United States Patent [19]

Dekeyser et al.

[11] Patent Number: 5,804,579
[45] Date of Patent: Sep. 8, 1998

[54] INSECTICIDAL OXADIAZINE COMPOUNDS

[75] Inventors: Mark Achiel Dekeyser, Waterloo, Canada; Paul Thomas McDonald, Middlebury, Conn.

[73] Assignees: Uniroyal Chemical Company, Inc., Middlebury, Conn.; Uniroyal Chemical Co./CIE., Elmira, Canada

[21] Appl. No.: 950,609

[22] Filed: Oct. 14, 1997

Related U.S. Application Data

[63] Continuation-in-part of Ser. No. 791,217, Jan. 20, 1997, abandoned.

[51] Int. Cl.$^6$ .......................... H01N 43/88; C07D 273/04
[52] U.S. Cl. ............................................ 514/229.2; 544/66
[58] Field of Search ............................ 544/66; 514/229.2

[56] References Cited

U.S. PATENT DOCUMENTS 5,677,301  10/1997  Dekeyser et al. .................... 514/229.2

*Primary Examiner*—Richard L. Raymond
*Attorney, Agent, or Firm*—Daniel Reitenbach

[57] ABSTRACT

Insecticidal substituted oxadiazines having the formula:

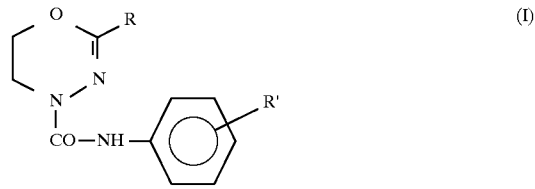

wherein R is an optionally substituted $C_4$–$C_5$ heterocyclic group and R' is hydrogen, halogen, $C_1$–$C_4$ haloalkyl or $C_1$–$C_4$ haloalkoxy, insecticidal compositions containing these oxadiazines, and methods for their use.

19 Claims, No Drawings

INSECTICIDAL OXADIAZINE COMPOUNDS

This is a continuation-in-part of U.S. application Ser. No. 08/791,217, filed on Jan. 30, 1997, now abandoned.

FIELD OF THE INVENTION

This invention relates to insecticidal substituted oxadiazine compounds, insecticidal compositions containing the oxadiazine compounds, and methods for their use.

BACKGROUND OF THE INVENTION

Certain oxadiazine compounds have been described as useful as pesticides and as pharmaceutical agents. For example, U.S. Pat. No. 5,536,720 describes substituted 2-phenyl-1,3,4-oxadiazine-4-carbamide compounds useful as insecticides and acaricides. Trepanier et al, J. Med. Chem 9:753–758 (1966) describe certain 2-substituted 4H-1,3,4-oxadiazines useful as anticonvulsants in mice. U.S. Pat. No. 3,420,826 describes certain 2,4,6-substituted 4H-1,3,4-oxadiazines, useful as sedatives, anticonvulsants, and as pesticides against nematodes, plants, and fungi. U.S. Pat. No. 3,420,825 describes methods for producing certain 2,4,6-substituted 4H-1,3,4-oxadiazines.

It is a purpose of this invention to provide novel oxadiazine derivatives useful as insecticides.

SUMMARY OF THE INVENTION

The present invention relates to a compound having the formula:

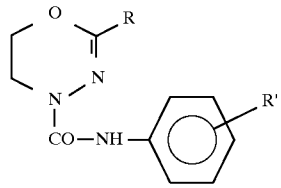

(I)

wherein R is a $C_4$–$C_5$ heterocyclic group comprising one nitrogen, sulfur, or oxygen atom, wherein the heterocyclic group can be unsubstituted or substituted with 1 to 3 halogen atoms or a $C_1$–$C_4$ haloalkyl group; and R' is hydrogen, halogen, $C_1$–$C_4$ haloalkyl or $C_1$–$C_4$ haloalkoxy. These compounds, or physiologically acceptable salts thereof, are useful as insecticides.

The insecticidal compositions of this invention comprise: (a) an effective amount of one or more compounds of formula I, and (b) a suitable carrier.

DETAILED DESCRIPTION OF THE INVENTION

Preferably, the compound of this invention has the formula:

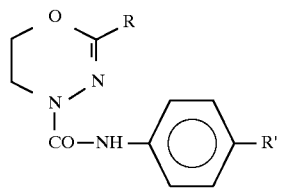

(IA)

Preferably, R is an aromatic heterocyclic group, more preferably, a thienyl, furanyl, or pyridinyl group, optionally substituted by 1 to 3 bromo or chloro atoms, more preferably, one bromo or one chloro, or by $C_1$–$C_4$ trihaloalkyl, more preferably, trihalomethyl, trihaloethyl, trihalomethoxy or trihaloethoxy; and R' is $C_1$–$C_4$ trihaloalkyl or $C_1$–$C_4$ trihaloalkoxy, more preferably, trihalomethyl, trihaloethyl, trihalomethoxy or trihaloethoxy. Particularly preferred is the compound of formula I wherein R is thienyl, furanyl or pyridinyl, substituted by bromo or chloro, and R' is trihalomethoxy or trihalomethyl. Most preferred is the compound of formula I wherein R is 5-bromo-2-thienyl, 5-chloro-2-thienyl, 5-bromo-3-pyridinyl, or 5-bromo-2-furanyl, and R' is trifluoromethoxy or trifluoromethyl.

The compounds and compositions of this invention are useful as plant protecting agents against insects and are particularly effective against coleopterous insects and lepidopterous insects, such as tobacco budworm.

The compounds of the instant invention can be prepared by reacting an oxadiazine of formula A below, wherein R is described above, with an isocyanate of formula B below, wherein R' is described above, and a catalytic amount of triethylamine in a suitable solvent such as acetonitrile or toluene.

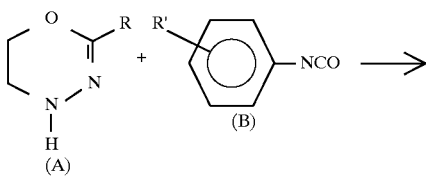

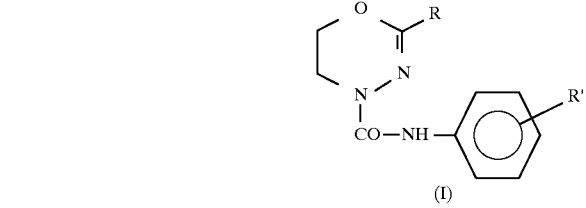

Compounds of formula A above can be prepared by reacting a hydrazide of the formula

R—CO—NH—NH$_2$    (C)

wherein R is as described above, with 1-bromo-2-fluoroethane (BrCH$_2$CH$_2$F), in the presence of a base. Such bases include alkali metal hydroxides. Preferred bases include sodium or potassium hydroxide.

The compositions of the present invention can be prepared by formulating one or more compounds of the present invention with a suitable carrier.

Suitable liquid carriers can comprise water, alcohols, ketones, phenols, toluene and xylenes. In such formulations, additives conventionally employed in the art can be utilized, such as one or more surface active agents and/or inert diluents, to facilitate handling and application of the resulting insecticidal composition.

Alternatively, the compounds of this invention can be applied as a liquid or in sprays when utilized in a liquid carrier, such as a solution comprising a compatible solvent such as acetone, benzene, toluene or kerosene, or a dispersion comprising a suitable non-solvent medium such as water.

The compositions of this invention can alternatively comprise solid carriers taking the form of dusts, granules, wettable powders, pastes, aerosols, emulsions, emulsifiable concentrates, and water-soluble solids. For example, the compounds of this invention can be applied as dusts when admixed with or absorbed onto powdered solid carriers, such as mineral silicates, talc, pyrophyllite and clays, together with a surface-active dispersing agent so that a wettable powder is obtained which then is applied directly to the loci to be treated. Alternatively, the powdered solid carrier containing the compound admixed therewith, can be dispersed in water to form a suspension for application in such form.

Granular formulations of the compounds are preferred for field treatment and are suitable for application by broadcasting, side dressing, soil incorporation or seed treatment, and are suitably prepared using a granular or pelletized form of carrier such as granular clays, vermiculite, charcoal or corn cobs. The compound of this invention is dissolved in a solvent and sprayed onto an inert mineral carrier such as attapulgite granules (10–100 mesh), and the solvent is then evaporated. Such granular compositions can contain from 2–25% of a compound of this invention, based on carrier plus compound, preferably, 3–15%. In addition, the compounds of this invention can also be incorporated into a polymeric carrier such as polyethylene, polypropylene, butadiene-styrene, styrene-acrylonitrile resins, polyamides, poly(vinyl acetates), and the like. When encapsulated, the compound of this invention can advantageously be released over an even longer time period, extending its effectiveness further than when used in non-encapsulated form.

Another method of applying the compound of this invention to the loci to be treated is by aerosol treatment, for which the compound can be dissolved in an aerosol carrier which is a liquid under pressure but which is a gas at ordinary temperature (e.g., 20° C.) and atmospheric pressure. Aerosol formulations can also be prepared by first dissolving the compound in a less volatile solvent and then admixing the resulting solution with a highly volatile liquid aerosol carrier.

For treatment of plants (such term including plant parts), the compounds of the invention preferably are applied in aqueous emulsions containing a surface-active dispersing agent which can be non-ionic, cationic or anionic. Suitable surface-active agents are well known in the art, such as those disclosed in U.S. Pat. No. 2,547,724 (columns 3 and 4). The compounds of this invention can be mixed with such surface-active dispersing agents, with or without an organic solvent, as concentrates for the subsequent addition of water, to yield aqueous suspensions of the compounds at desired concentration levels.

In addition, the compounds can be employed with carriers which themselves are pesticidally active, such as insecticides, acaricides, fungicides or bactericides.

It will be understood that the effective amount of a compound in a given formulation will vary depending, e.g., upon the specific pest to be combated, as well as upon the specific chemical composition and formulation of the compound being employed, the method of applying the compound/formulation and the locus of treatment. Generally, however, the effective amount of the compound of this invention can range from about 0.1 to about 95 percent by weight. Spray dilutions can be as low as a few parts per million, while at the opposite extreme, full strength concentrates of the compound can be usefully applied by ultra low volume techniques. When plants constitute the loci of treatment, concentration per unit area can range between about 0.01 and about 50 pounds per acre, with concentrations of between about 0.1 and about 10 pounds per acre preferably being employed for crops such as corn, tobacco, rice and the like.

To combat insects, sprays of the compounds can be applied to any suitable locus, such as to the insects directly and/or to plants upon which they feed or nest. The compositions of this invention can also be applied to the soil or other medium in which the pests are present.

The specific methods of application of the compounds and compositions of this invention, as well as the selection and concentration of these compounds, will vary depending upon such circumstances as crops to be protected, geographic area, climate, topography, plant tolerance, etc.

The following examples are provided to illustrate the present invention.

EXAMPLES

Example 1

Preparation of 5,6-dihydro-2-(5-bromo-2-thienyl)-4H-1,3,4-oxadiazine

A solution of 2.9 g (0.07 mole) sodium hydroxide dissolved in 10 ml of water was added dropwise at room temperature to a mixture of 6.5 g (0.03 mole) 5-bromo-2-thiophenecarboxylic acid hydrazide and 4.0 g (0.03 mole) 1-bromo-2-fluoroethane in 25 ml of ethanol. The resulting reaction mixture was refluxed for two and one-half hours. The reaction mixture was then cooled to room temperature, diluted with 150 ml of water and extracted several times with dichloromethane (100 ml). After separation and drying over anhydrous sodium sulfate, the organic phase was filtered and evaporated under reduced pressure leaving 4.5 g of an oil (60% yield). The oil was purified by silica gel chromatography to produce 5,6-dihydro-2-(5-bromo-2-thienyl)-4H-1,3,4-oxadiazine, as an oil.

Example 2

Preparation of 5,6-dihydro-N-[4-(trifluoromethoxy)-phenyl]-2-(5-bromo-2-thienyl)-4H-1,3,4-oxadiazine-4-carboxamide (Compound No. 1)

To 3 g of 5,6-dihydro-2-(5-bromo-2-thienyl)-4H-1,3,4-oxadiazine dissolved in 50 ml of acetonitrile, was added 2.5 g of 4-(trifluoromethoxy)phenyl isocyanate followed by two drops of triethylamine.

After this addition was complete, the resulting mixture was heated to reflux for 4 hours, and then evaporated under reduced pressure leaving a solid residue. The solid residue was recrystallized from ethanol to produce 2.6 g of 5,6-dihydro-N-[4-(trifluoromethoxy)phenyl]-2-(5-bromo-2-thienyl)-4H-1,3,4-oxadiazine-4-carboxamide, as an off-white solid, mp 139°–140° C.

The remaining compounds in Table 1 were prepared using essentially the same process. Each of the compounds is characterized by its NMR data.

TABLE 1

Structure:
$$\text{cyclic: O=C(R)-N=N(CO-NH-C_6H_4-R')}$$

| No | R | R' | NMR Data (ppm) In DMSO |
|----|---|----|-----------------------|
| 1 | 5-Br-2-C$_4$H$_2$S | OCF$_3$ | m(2)3.8–4.1, m(2)4.4–4.6, m(6)7.2–8.0, s(1)9.4 |
| 2 | 5-Br-2-C$_4$H$_2$O | OCF$_3$ | m(2)3.8–4.1, m(2)4.5–4.7, m(6)7.2–8.0, s(1)9.5 |
| 3 | 5-Cl-2-C$_4$H$_2$S | CF$_3$ | m(2)3.8–4.1, m(2)4.4–4.6, m(6)7.2–8.0, s(1)9.4 |
| 4 | 5-Cl-2-C$_4$H$_2$S | OCF$_3$ | m(2)3.8–4.1, m(2)4.4–4.6, m(6)7.1–7.9, s(1)9.1 |
| 5 | 5-Br-3-C$_6$H$_3$N | CF$_3$ | m(2)3.8–4.1, m(2)4.5–4.7, m(7)7.6–9.2, s(1)9.6 |
| 6 | 5-Br-3-C$_6$H$_3$N | OCF$_3$ | m(2)3.8–4.1, m(2)4.4–4.6, m(7)7.2–9.2, s(1)9.5 |

Example 3

Stock Solution Preparation

The remaining examples relate to the insecticidal use of the compounds of this invention. In all these examples, a stock solution for the compounds was prepared at 3000 ppm by dissolving 0.24 gram of each compound to be tested in 8 ml of acetone and adding 72 ml of distilled water plus 3 drops of ethoxylated sorbitan monolaurate, a wetting agent. This stock solution was used in the remaining examples demonstrating the insecticidal use of representative compounds of this invention. For each example that follows, this stock solution was used and the specificized dilutions made. All the tests discussed below, which involved treatment with compounds of this invention were always repeated with controls, in which the active compound was not provided, to permit a comparison upon which the percent control was calculated.

Example 4

Southern Corn Rootworm Test

The stock solution of 3000 ppm prepared in Example 2 above, was diluted to 100 ppm (test solution). For each compound, 2.5 ml of the test solution was pipetted onto a filter paper (Whatman #3) at the bottom of a 100 mm petri dish. Two corn seedlings were soaked in the 100 ppm solution for 1 hour and transferred to the petri dish containing the same test solution. After 24 hours, each dish was loaded with 5 second instar larvae of Southern Corn Rootworm (*Diabrotica undecimpunctata*). After five days, the number of live larvae was noted and the percent control, corrected by Abbott's formula [see J. Economic Entomology 18:265–267 (1925)] was calculated.

The results of the testing of Southern Corn Rootworm (CR) are presented in Table 2 below.

Example 5

Rice Planthopper Foliar Test

The stock solution of 3000 ppm prepared in Example 2 above, was diluted to 1000 ppm. One pot containing approximately 20 Mars variety rice seedlings was treated with each formulation by spraying with a spray atomizer. One day after treatment plants were covered with a tubular cage and twenty adult rice delphacids, *Sogatodes orizicola*, were transferred into each cage. Five days after transferring, counts were made of the surviving planthoppers in each pot and percent control was estimated.

Results of the testing of rice planthoppers (RPH) are presented in Table 2 below.

Example 6

Tobacco Budworm Test

For each compound, 0.2 ml of the stock solution prepared in Example 2 above, was pipetted onto the surface of each of 5 diet cells, allowed to spread over the surfaces and air dried for two hours. Then a second instar *Helicoverpa virescens* larva was introduced into each cell. After 14 days, the number of living larvae was determined for each treatment and percent control, corrected by Abbott's formula, was calculated.

The results of the testing of tobacco budworms (TB) are presented in Table 2 below.

TABLE 2

PERCENT CONTROL OF SOUTHERN CORN ROOTWORM, RICE PLANTHOPPER AND TOBACCO BUDWORM

| Compound No. | Percent Control | | |
|---|---|---|---|
| | CR | RPH | TB |
| 1 | 100 | 0 | 100 |
| 2 | 100 | 0 | 100 |
| 3 | 100 | 0 | 100 |
| 4 | 100 | 0 | 100 |
| 5 | 80 | 0 | 100 |
| 6 | 57 | 80 | 100 |

What is claimed is:

1. A compound having the formula:

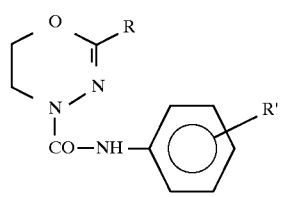

(I)

wherein R is a C$_4$–C$_5$ heterocyclic group comprising one nitrogen, sulfur, or oxygen atom, wherein the heterocyclic group can be unsubstituted or substituted with 1 to 3 halogen atoms or a C$_1$–C$_4$ haloalkyl group; and R' is hydrogen, halogen, C$_1$–C$_4$ haloalkyl or C$_1$–C$_4$ haloalkoxy.

2. A compound as recited in claim 1 having the formula:

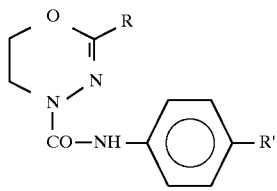

(IA)

wherein R is a $C_4$–$C_5$ heterocyclic group comprising one nitrogen, sulfur, or oxygen atom, wherein the heterocyclic group can be unsubstituted or substituted with 1 to 3 halogen atoms or a $C_1$–$C_4$ haloalkyl group; and R' is $C_1$–$C_4$ haloalkyl or $C_1$–$C_4$ haloalkoxy.

3. A compound as recited in claim 2 wherein R is an aromatic heterocyclic group, unsubstituted or substituted with 1 to 3 halogen atoms or a $C_1$–$C_4$ haloalkyl group.

4. A compound as recited in claim 3 wherein R is a thienyl, furanyl, or pyridinyl group, unsubstituted or substituted with 1 to 3 halogen atoms or a $C_1$–$C_4$ haloalkyl group.

5. A compound as recited in claim 4 wherein R is a thienyl, furanyl, or pyridinyl group, substituted by 1 to 3 bromo or chloro atoms.

6. A compound as recited in claim 5 wherein R is a thienyl, furanyl, or pyridinyl group, substituted by one bromo or one chloro.

7. A compound as recited in claim 4 wherein R is a thienyl, furanyl, or pyridinyl group, substituted by $C_1$–$C_4$ trihaloalkyl or $C_1$–$C_4$ trihaloalkoxy.

8. A compound as recited in claim 7 wherein R is a thienyl, furanyl, or pyridinyl group, substituted by trihalomethyl, trihaloethyl, trihalomethoxy or trihaloethoxy.

9. A compound as recited in claim 4 wherein R' is $C_1$–$C_4$ trihaloalkyl or $C_1$–$C_4$ trihaloalkoxy.

10. A compound as recited in claim 9 wherein R' is trihalomethyl, trihaloethyl, trihalomethoxy or trihaloethoxy.

11. A compound as recited in claim 10 wherein R' is trifluoromethoxy or trifluoromethyl.

12. A compound as recited in claim 1 having the formula:

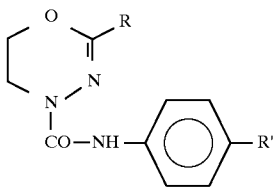

(IA)

wherein R is thienyl, furanyl or pyridinyl, substituted by bromo or chloro, and R' is trihalomethoxy or trihalomethyl.

13. A compound as recited in claim 12 wherein R is 5-bromo-2-thienyl, 5-chloro-2-thienyl, 5-bromo-3-pyridinyl, or 5-bromo-2-furanyl, and R' is trifluoromethoxy or trifluoromethyl.

14. An insecticidal composition comprising an effective amount of a compound as recited in claim 1 and a suitable carrier.

15. An insecticidal composition comprising an effective amount of a compound as recited in claim 2 and a suitable carrier.

16. An insecticidal composition comprising an effective amount of a compound as recited in claim 12 and a suitable carrier.

17. A method for controlling insects which comprises applying to a locus to be protected, an effective amount of a compound as recited in claim 1.

18. A method for controlling insects which comprises applying to a locus to be protected, an effective amount of a compound as recited in claim 2.

19. A method for controlling insects which comprises applying to a locus to be protected, an effective amount of a compound as recited in claim 12.

* * * * *